(12) United States Patent
Holmström

(10) Patent No.: US 6,618,621 B1
(45) Date of Patent: Sep. 9, 2003

(54) PACEMAKER WITH STIMULATION THRESHOLD MEASURING

(75) Inventor: Nils Holmström, Järfälla (SE)

(73) Assignee: St. Jude Medical AB, Järfälla (SE)

(*) Notice: Subject to any disclaimer, the term of this patent is extended or adjusted under 35 U.S.C. 154(b) by 0 days.

(21) Appl. No.: 09/701,259

(22) PCT Filed: May 12, 1999

(86) PCT No.: PCT/SE99/00813
§ 371 (c)(1),
(2), (4) Date: Jan. 10, 2001

(87) PCT Pub. No.: WO99/61102
PCT Pub. Date: Dec. 2, 1999

(30) Foreign Application Priority Data

May 27, 1998 (SE) .................................................. 9801880

(51) Int. Cl.[7] .................................................. A61N 1/18
(52) U.S. Cl. ......................................................... 607/28
(58) Field of Search ................................. 607/28, 9, 11, 607/27

(56) References Cited

U.S. PATENT DOCUMENTS

| | | |
|---|---|---|
| 4,979,507 A | 12/1990 | Heinz et al. |
| 5,391,191 A | 2/1995 | Holmström |
| 5,447,525 A | 9/1995 | Powell et al. |
| 5,683,431 A | 11/1997 | Wang |
| 5,697,956 A * | 12/1997 | Bornzin ....................... 607/28 |

* cited by examiner

*Primary Examiner*—Mark Bockelman
(74) *Attorney, Agent, or Firm*—Schiff Hardin & Waite

(57) ABSTRACT

A pacemaker has a stimulation threshold measuring unit which measures a stimulation threshold voltage value of a heart and a pulse generator for deliverying stimulation pulses of variable amplitudes and durations to the heart. The pulse generator is controlled by a control unit to deliver the stimulation pulses with respective amplitudes related to the measured threshold value and a safety margin. The control unit automatically changes the safety margin in accordance with a predetermined relationship between the safety margin and the measured threshold value, so that the safety margin is progressively increased as the measured threshold value increases.

3 Claims, 3 Drawing Sheets

PACEMAKER WITH STIMULATION THRESHOLD MEASURING

This application is a 371 of PCT/SE99/00813 filed May 21, 1999.

BACKGROUND OF THE INVENTION

1. Field of the Invention

The present invention relates to a pacemaker of the type having stimulation threshold measuring means for measuring the stimulation threshold voltage value.

2. Description of the Prior Art

It is advantageous to use stimulation pulses of short pulse widths and corresponding high amplitudes which gives a low noise to signal ratio, since with such stimulation pulses the pacemaker current consumption is lower, which results in an increased lifetime of the pacemaker battery, and the polarization is reduced, which e.g. facilitates the detection of evoked response. Thus, it is preferable to use short stimulation pulses as long as the associated stimulation amplitude is below the battery voltage, i.e. as long as voltage doublers are not needed, of U.S. Pat. No. 5,391,191.

Since numerous factors have a changing influence on the stimulation threshold the stimulation must be performed with a safety margin. A 100% safety margin was previously manually set, which means that the energy delivered for pacing was 100% higher than the minimum amount of energy necessary for exciting the heart at the time of control. This known technique is illustrated in FIG. 1a for a constant pulse width.

In automatically threshold searching pacemakers of today stimulation pulses are normally delivered with an amplitude equal to the stimulation threshold value $U_{thres}$ plus a safety margin m, thus $$U_{stim}=U_{thres}+m \quad (1)$$

If a constant safety margin of e.g. 0.3V is used (which is illustrated in FIG. 1b), independent of the threshold value $U_{thres}$, this safety margin is relatively smaller for high amplitude pulses than for pulses of lower amplitudes. This means that when using short stimulation pulses with corresponding high amplitudes, loss of capture occurs frequently and results in several back-up pulses and triggered threshold searches, which disturbs the proper function of the pacemaker.

U.S. Pat. No. 4,979,507 deals with the problem of controlling the pacemaker pulse energy in operation most efficiently to prolong battery life by matching of individual patient pacemaker-implant electrode interface to follow dynamic changes occurring in use. It is then shown that the stimulation energy consumption is lowest for pulse widths corresponding to chronaxie of the strength-duration characteristic. The stimulation threshold at the time of chronaxie is determined by a two point measurement and is continuously checked and the stimulation is prescribed to be performed with an added safety margin in the range of 5–30%. This safety margin can be added by elevating either the voltage amplitude or the pulse width, the latter being preferred according to this patent. Thus a conventional safety margin is added to the threshold value determined at the chronaxie to achieve the lowest energy.

Also U.S. Pat. No. 5,447,525 deals with the problem of minimizing current drain while maintaining a desired capture safety margin. Either periodically or as a result of a loss of capture, the pacemaker then calculates for each possible width a threshold value based upon 10 the measured rheobase and derived chronaxie. Each threshold value is multiplied by a pre-determined safety margin. As pacing stimulation signal is then the voltage-pulse width pair chosen having the lowest current drain and satisfying the desired safety margin.

SUMMARY OF THE INVENTION

An object of the present invention is to reduce the number of losses of capture by a new and reliable technique which avoids the disadvantages of known manners of adding a safety margin.

The above object is achieved in accordance with the principles of the present invention in a pacemaker having a stimulation threshold measuring arrangement for measuring the stimulation threshold value, a unit for generating a safety margin, and a pulse generator for deliverying stimulation pulses of variable amplitudes and duration under the control of a control unit which sets the amplitudes dependent on the measured threshold value and the safety margin, wherein the unit for generating a safety margin automatically changes the safety margin in accordance with a predetermined relationship between the safety margin and the measured threshold value, this relationship being such that the safety margin is progressively increased when the measured threshold value increases.

Thus, with a pacemaker according to the invention, stimulation pulses are delivered, which are progressively increasing with increasing values of the measured threshold value for the actual pulse duration, i.e. a dynamically adjustable safety margin is provided, which is based on threshold measurements and is progressively increasing with increasing threshold value.

In a embodiment of the pacemaker according to the invention said safety margin generating means is adapted to increase and decrease the magnitudes of the safety margin m in predetermined steps, when the threshold value is increased above and decreased below predetermined threshold limit values. By limiting the safety margin to only a limited number of steps the electronics of the safety margin generating means can be simplified, yet a considerable improvement of the proper functioning of the pacemaker is obtained vis-a-vis use of a constant safety margin. Even if the safety margin is varied between only two prescribed level the number of losses of capture is considerably reduced compared to a situation of a constant safety margin.

DESCRIPTION OF THE PREFERRED EMBODIMENTS

Figure 1A:
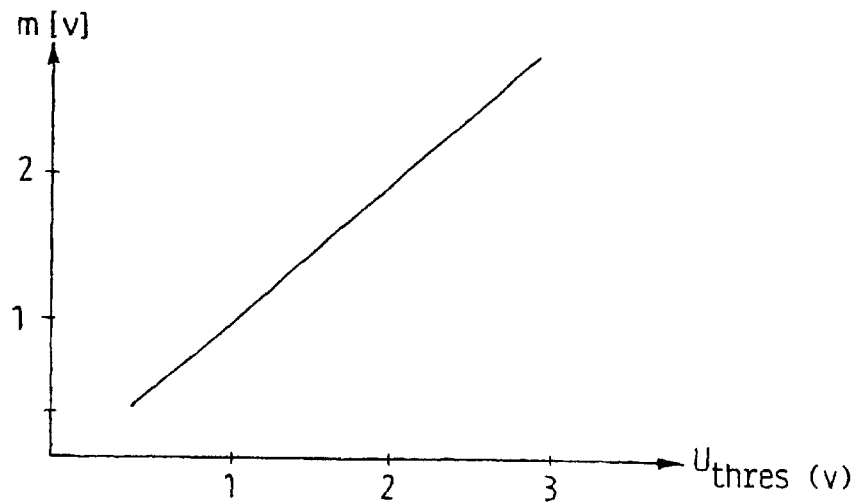
FIGS. 1a and 1b are respective diagrams illustrating the relationship between the safety margin and the stimulation threshold, as is known.
Figure 1B:
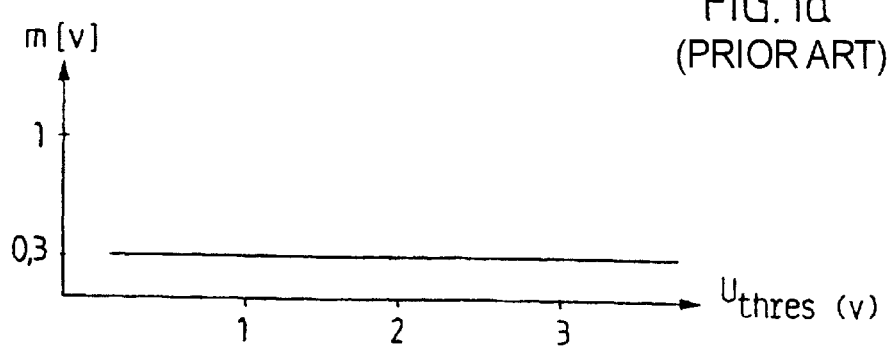
Figure 2:
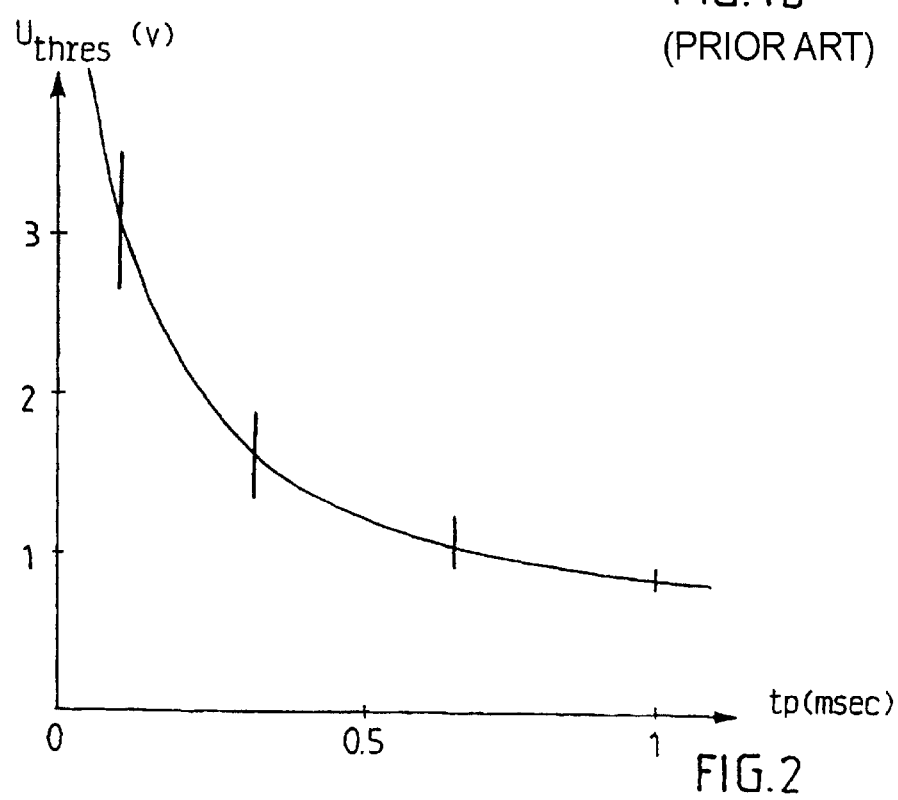
FIG. 2 is an amplitude strength-duration curve for a typical stimulation electrode.

FIG. 2 is the amplitude strength-duration curve showing the stimulation threshold value $U_{thres}$ as a function of the pulse width tp for a typical pacemaker electrode. The stimulation threshold $U_{thres}$ is naturally varying with the breathing, circadian variations, coughing, straining etc. These variations in the threshold amplitude $U_{thres}$ are illustrated in the figure by vertical bars. To avoid that such natural variations result in loss of capture the stimulation must be performed with a certain safety margin.

Figure 3:
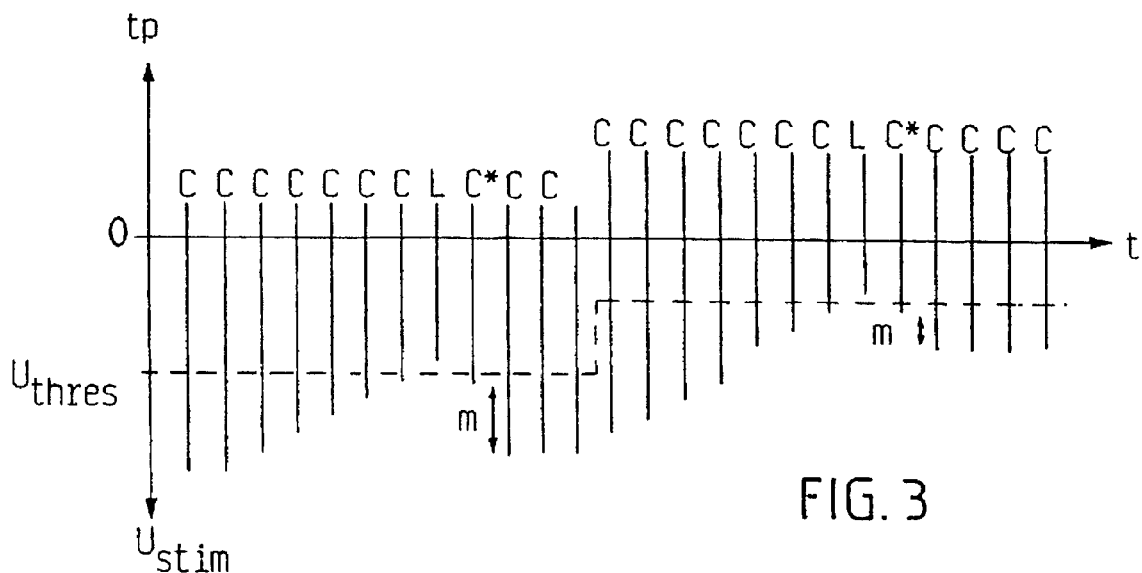
FIG. 3 is a diagram illustrating stimulation threshold searches at two different pulse widths.

Several losses of capture also result in several stimulation threshold searches. If for instance two consecutive losses of capture are detected a threshold search is automatically started to find out if there are changes which cause the losses. A threshold search algorithm is then automatically stepping down the stimulation amplitude $U_{stim}$ till the threshold $U_{thres}$ is reached. This is illustrated in FIG. 3 which illustrates threshold searches at two different pulse width tp. Each vertical bar represents one step in the stepping down procedure, the length of the bar above the horizontal t-axis representing the pulse width tp and length of the bar below this horizontal axis representing the pulse amplitude $U_{stim}$. C indicates that capture is detected, L indicates loss of capture and C* denotes the measured threshold value.

From the FIG. 3 appears that for a short stimulation pulse the stimulation threshold $U_{thres}$ is higher than for a wider pulse. The safety margin m is larger for a higher threshold value $U_{thres}$.

In the example shown in FIG. 3 safety margins of two different magnitudes are related to two different threshold value $U_{thres}$. The safety margin needs, however not be a continuous increasing function with increasing $U_{thres}$. In practice excellent results will be obtained also with digitised safety margins. Thus if e.g. 3–4 safety margin levels are used, each level being related to a corresponding threshold interval, the electronics of the safety margin generating means can be simplified considerably. The steps of the safety margin can typically be 0.3 V, that is the voltage safety margin can be 0.3V for a first threshold interval, 0.6 V for a second threshold interval, etc. A higher resolution and better accuracy can of course be obtained by reducing the safety margin step to e.g. 0.1 V.

Figure 4A:
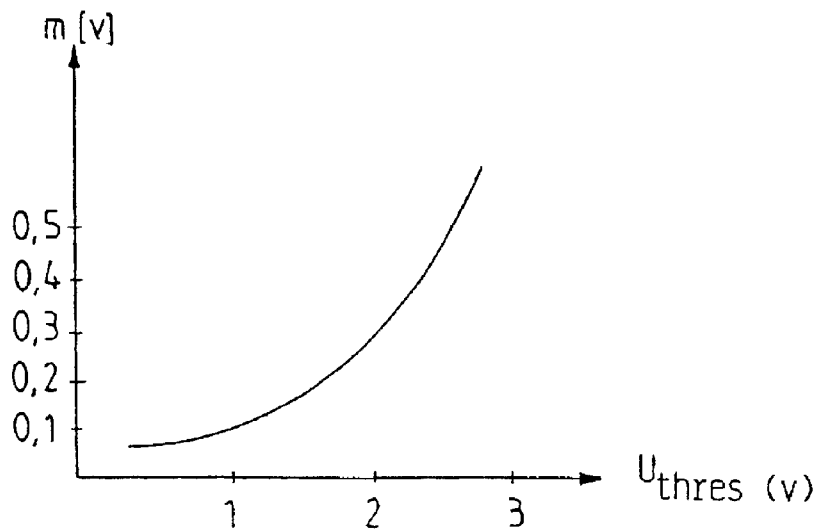
FIGS. 4a, 4b and 4c are respective diagrams illustrating the relationship between the safety margin and the stimulation threshold according to three preferred embodiments of the invention.
Figure 4B:
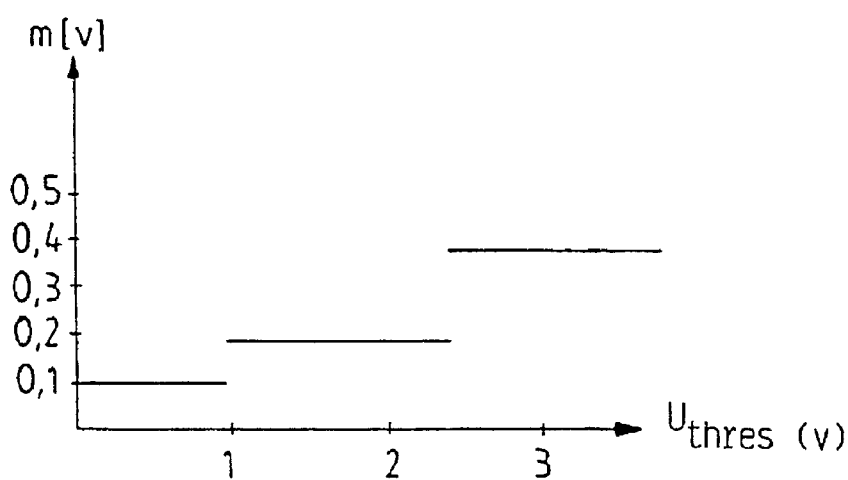
Figure 4C:
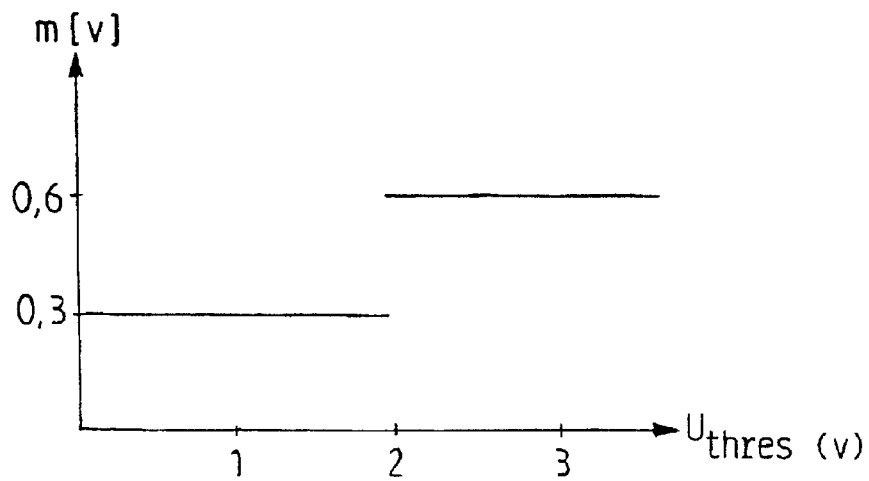

Diagrams disclosing three preferred embodiments of the invention are shown in FIGS. 4a, 4b and 4c. In the first preferred embodiment disclosed in FIG. 4a the safety margin m continuously increases progressively in relation to the measured stimulation threshold $U_{thres}$. In the diagram the measured threshold is shown on the X-axis and the safety margin on the Y-axis. The invention is illustrated by a curve which has an increasing first derivate in a region defined by values of the measured stimulation thresholds between a predetermined lower limit, e.g. 0.3 Volts and a predetermined higher limit, e.g. 4 Volts. These values of the higher and lower limits are chosen in relation to how the values of the measured threshold values vary in practise. The curve could e.g. be describe as a part of a parable-like curve, i.e. the safety margin is approximately the sum of a first constant and the square of the measured threshold value multiplied by a second constant.

In the second and third preferred embodiments shown in FIGS. 4b and 4c respectively the safety margin m instead are step-wise progressively increased. In the diagrams in FIG. 4b and 4c three and two steps are shown respectively. The embodiment illustrated in FIG. 4b has a safety margin m of 0.1 Volts for stimulation thresholds below 1 Volts; 0.2 Volts for stimulation thresholds between 1 and 2.5 Volts, and a safety margin of 0.3 Volts for stimulation thresholds above 2.5 Volts. The embodiment illustrated in FIG. 4c has a safety margin m of 0.3 Volts for stimulation thresholds below 2 Volts and 0.6 Volts for stimulation thresholds above 2 Volts. The number of steps could of course be chosen to any value greater than one.

It should be noted that each diagram represents the situation for a constant pulse width (pulse duration). The pulse width can of course be changed e.g. in accordance with information obtained from the strength duration curve.

Figure 5:
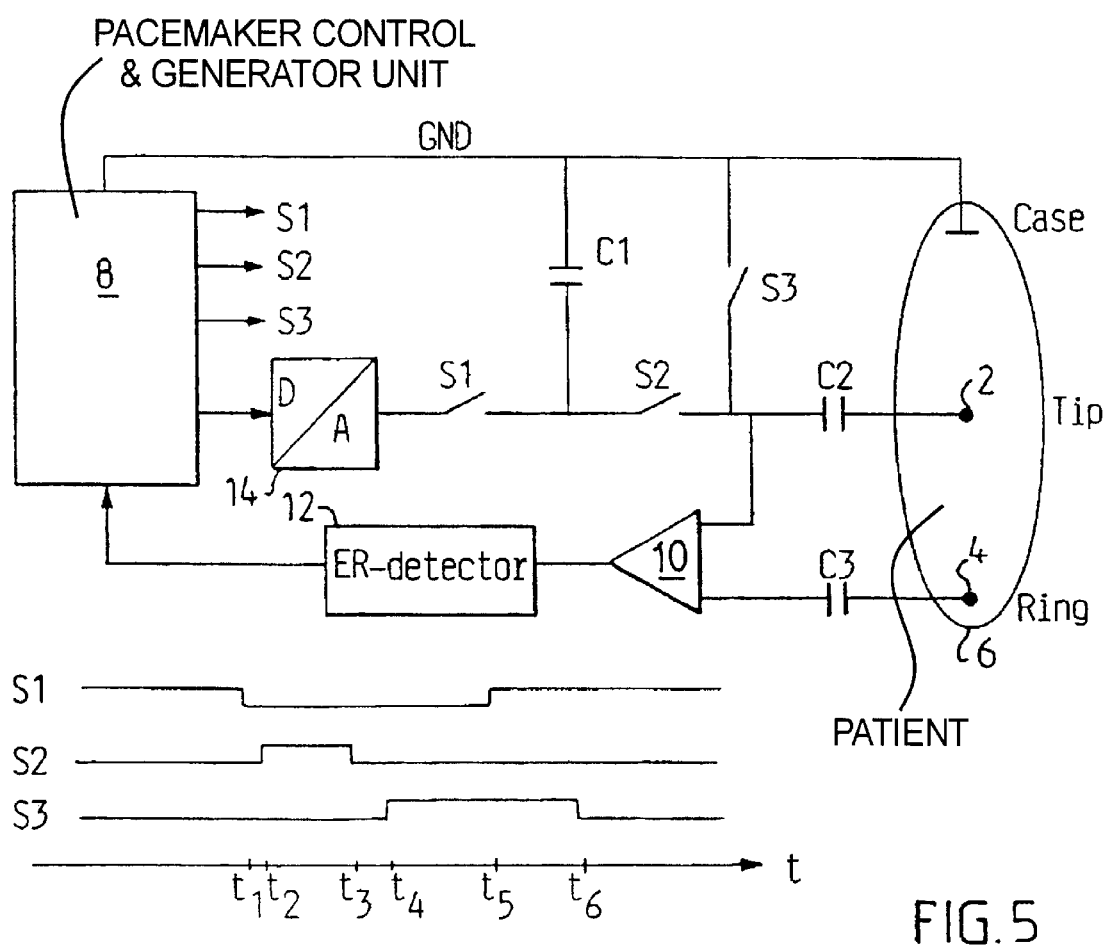
FIG. 5 is a block diagram of the output stage of a pacemaker constructed and operating in accordance with the principles of the present invention.

FIG. 5 is a block diagram showing the output stage of a pacemaker according to the invention. Timing diagrams are also included to illustrate the functioning of the output stage.

The pacemaker is connected through its output stage to tip and ring electrodes 2, 4 implanted in a patient 6. The case of the pacemaker is defining ground potential. From the pacemaker control and generator unit 8 the switches S1, S2 and S3 are controlled from corresponding outputs. In the time interval $t_5$–$t_1$ the switch S1 is closed and the switch S2 is open and the capacitor C1 is charged via the DA-converter 14 to the stimulation amplitude determined from control and generator unit 8. At time $t_1$ the switch S1 is opened and at time $t_2$ the switch S2 is closed and a stimulation pulse is delivered to the electrode tip 2 through the capacitor C2 during the interval $t_2$–$t_3$. After the delivery of a stimulation pulse the switch S3 is closed in time interval $t_4$–$t_6$ to connect the capacitor C2 and one of the inputs to amplifier 10 preceding the evoked response detector 12 to ground.

Through the capacitor C3 and the amplifier 10 the response of the heart to the delivered stimulation pulse is supplied to the evoked response detector 12 for detecting whether evoked response is obtained or not. The output signal from the evoked response detector 12 is supplied to the pacemaker control and generator unit 8 to indicate whether capture is detected or not for possible change of the stimulation pulse amplitude.

The safety margin as described above is generated in the unit 8 to determine the actual amplitude of the stimulation pulse to be delivered.

As discussed above the safety margin can suitably be varied only in a limited number of steps in order to simplify the electronics of the pacemaker control and generator unit 8 for the safety margin generation. Thus if e.g. a stimulation threshold of 1.2 V is measured for a pulse width of 0.5 ms a safety margin of 0.2 V could be suitable. If the pulse is reduced to 0.2 ms the corresponding threshold value can be 2.0 V and the safety margin can be chosen to 0.6 V.

Although modifications and changes may be suggested by those skilled in the art, it is the intention of the inventor to embody within the patent warranted hereon all changes and modifications as reasonably and properly come within the scope of his contribution to the art.

I claim:

1. A pacemaker comprising:
   a stimulation threshold measuring unit for measuring a stimulation threshold voltage value of a heart;
   a pulse generator for emitting stimulation pulses respectively having variable amplitudes and durations; and
   a control unit connected to said pulse generator for setting the respective amplitudes of said stimulation pulses dependent on said threshold voltage value and a safety margin, said control unit automatically changing said safety margin in accordance with a predetermined relationship between said safety margin and said threshold voltage value, to progressively increase said safety margin relative to said threshold voltage value as said threshold voltage value increases.

2. A pacemaker as claimed in claim 1 wherein said control unit increases said safety margin in respective predetermined steps as said threshold voltage value successively increases above successive predetermined, upwardly progressing threshold limit values, and decreases said safety margin in successive predetermined steps as said threshold voltage value successively decreases below successive predetermined decreasing threshold limit values.

3. A pacemaker as claimed in claim 1 wherein said control unit changes said safety margin dependent on a stored curve representing said relationship having a first derivative in a region defined by values of said threshold voltage between approximately 0.3 volts and approximately four volts.

* * * * *